(12) United States Patent
Donley

(10) Patent No.: US 7,998,405 B2
(45) Date of Patent: Aug. 16, 2011

(54) PROTECTING THE EYES OF CONTACT LENS WEARERS

(76) Inventor: Keith K. Donley, Port Aransas, TX (US)

( * ) Notice: Subject to any disclaimer, the term of this patent is extended or adjusted under 35 U.S.C. 154(b) by 950 days.

(21) Appl. No.: 11/825,783

(22) Filed: Jul. 9, 2007

(65) Prior Publication Data
US 2008/0008619 A1  Jan. 10, 2008

Related U.S. Application Data

(60) Provisional application No. 60/819,092, filed on Jul. 7, 2006.

(51) Int. Cl.
*A61L 2/18* (2006.01)
(52) U.S. Cl. .......................... 422/28; 422/37
(58) Field of Classification Search .................. 422/28, 422/37
See application file for complete search history.

(56) References Cited

U.S. PATENT DOCUMENTS

| | | | |
|---|---|---|---|
| 2,565,872 A | 8/1951 | Melsheimer | |
| 3,402,747 A | 9/1968 | Tissot-Dudont | |
| 3,473,886 A | 10/1969 | Leeds | |
| 3,912,451 A | 10/1975 | Gaglia | |
| 4,011,941 A | 3/1977 | Parsons | |
| 4,169,124 A * | 9/1979 | Forstrom et al. | 422/33 |
| 4,207,287 A * | 6/1980 | Lindquist | 422/33 |
| 4,784,167 A | 11/1988 | Thomas | |
| 4,852,592 A * | 8/1989 | DiGangi et al. | 134/57 R |
| 4,905,819 A | 3/1990 | Clements | |
| 5,089,240 A | 2/1992 | Perlaky | |
| 5,127,517 A | 7/1992 | Clements | |
| 5,270,002 A | 12/1993 | Neff | |
| 5,897,833 A * | 4/1999 | Hunt et al. | 422/28 |
| 6,228,333 B1 | 5/2001 | Mueller-Lierheim | |

\* cited by examiner

*Primary Examiner* — Sean E Conley
(74) *Attorney, Agent, or Firm* — G. Turner Moller

(57) ABSTRACT

The eyes of a contact lens wearer are protected from the effects of a liquid disinfecting solution by providing a contact lens container having a catalyst therein and a container of the disinfecting solution of unusual design. The openings of the contact lens container and the solution container are configured so only the contact lens container is able to receive solution from the solution container. This prevents the user from directly removing disinfecting solution from the solution container and thereby prevents the user from directly applying the disinfecting solution to the eye.

16 Claims, 3 Drawing Sheets

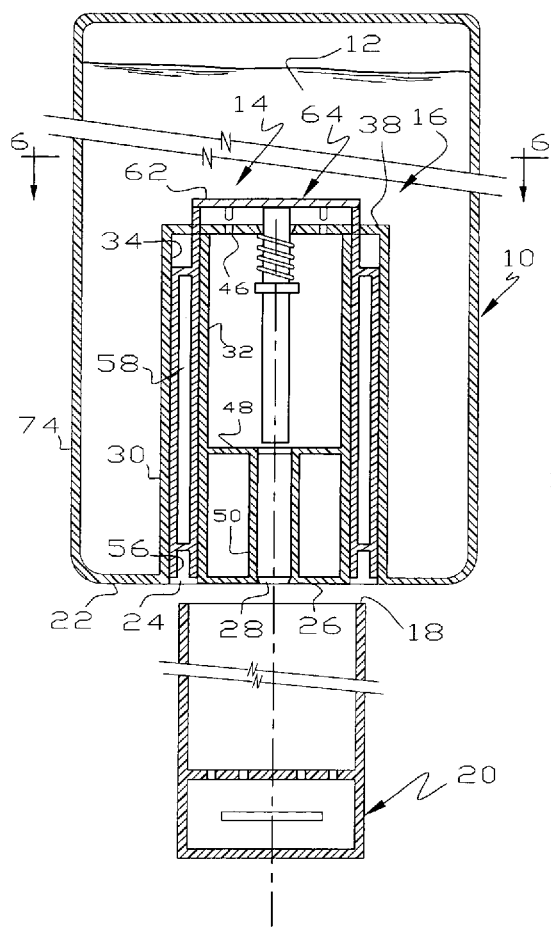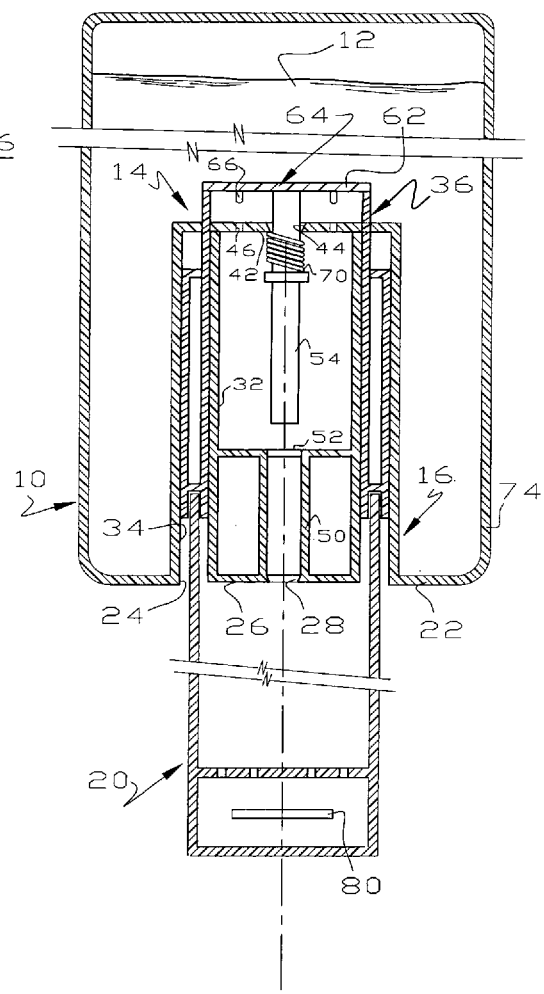

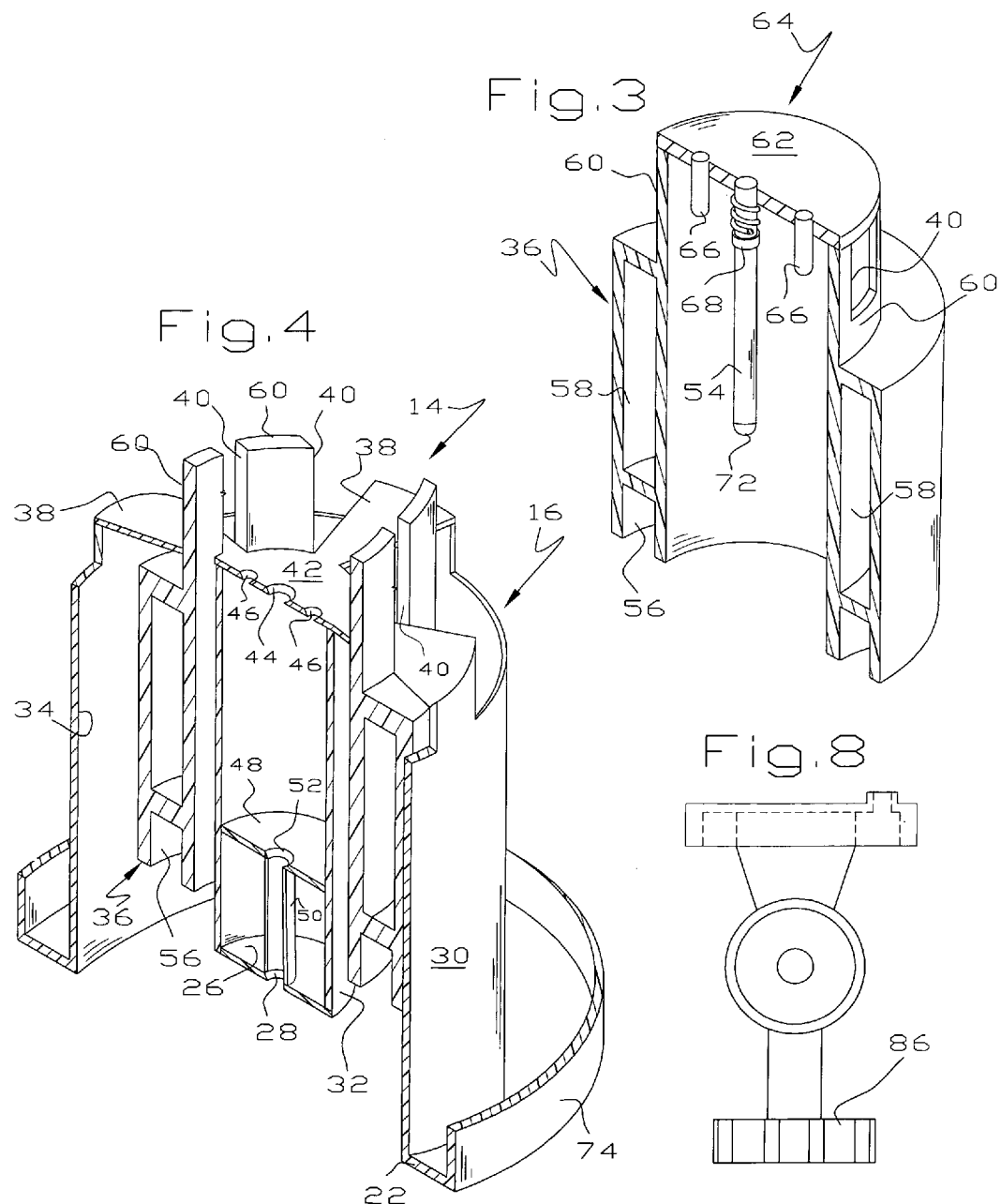

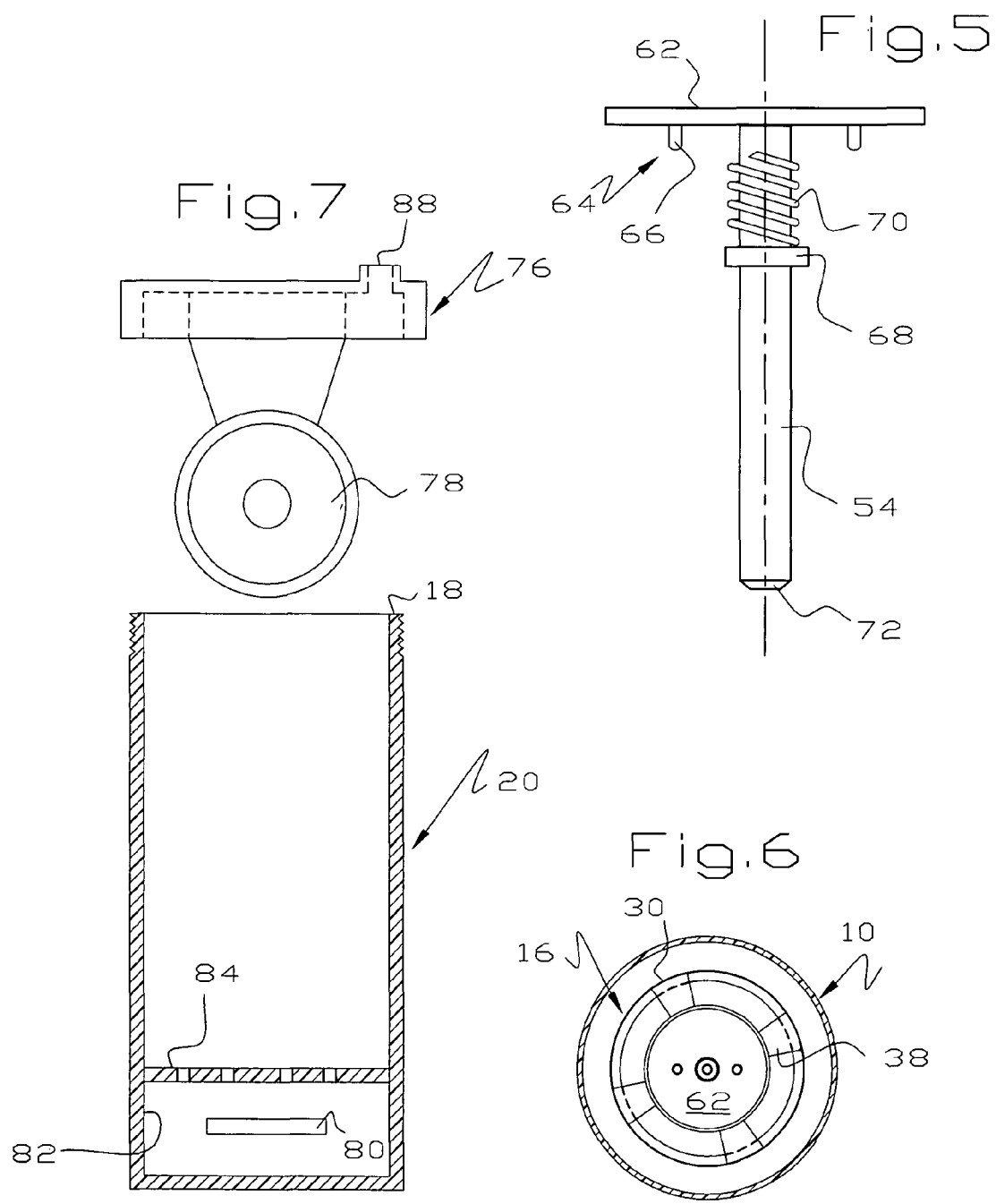

PROTECTING THE EYES OF CONTACT LENS WEARERS

This application is based on Provisional Application Ser. No. 60/819,092, filed Jul. 7, 2006, priority of which is hereby claimed.

This invention relates to an apparatus for and a method of protecting the eyes of the wearers of contact lenses from irritating liquid lens cleaning solutions and more particularly to a fool proof method and apparatus of transferring the irritating lens cleaning solution to a contact lens container.

BACKGROUND OF THE INVENTION

Contact lenses are commonly worn by many people. Currently, it is estimated that 125 million people world wide enjoy the comfort, convenience and cosmetic appearance that contact lenses provide. In order to receive these benefits, proper maintenance of contact lenses is necessary. Although some contact lenses are designed to be worn for a short period and then thrown away, it is more common for users to periodically disinfect contact lenses to reduce or eliminate harmful microorganisms such as fungi and bacteria. While disinfecting contact lenses, they are also cleaned of protein, lipid deposits and particulates that accumulate on the lenses.

To date, the single most effective method of disinfecting contact lenses is by immersing the lenses in an aqueous hydrogen peroxide solution. As suggested in U.S. Pat. No. 3,912,451, disinfecting with hydrogen peroxide is conveniently done in the presence of a catalyst so that the hydrogen peroxide is decomposed to produce water and gaseous oxygen. Hydrogen peroxide is a known effective disinfectant and, with one requirement recognized in the prior art, is eminently suitable for disinfecting contact lenses and is, in fact, the preferred disinfectant. The known requirement is that the hydrogen peroxide must be neutralized before the contact lens is reinserted into the user's eye. Otherwise, the hydrogen peroxide causes significant pain and discomfort and may potentially cause eye injury. The degree of pain and discomfort varies, given differences in individual sensitivity and variations in the strength of the hydrogen peroxide solution when exposed.

By placing the contact lens in a container having a catalyst therein, the hydrogen peroxide decomposes in a relatively predictable manner. Thus, placing the contact lens in the container, conveniently before retiring for the night, produces a neutralized solution by the next morning. This process, accelerated by the catalyst, reduces the hydrogen peroxide from a 3% or so solution to a 10-30 parts per million solution by morning. So far as is known, almost all users can tolerate a 10-30 parts per million solution and thus safely insert the contact lenses in their eyes.

It is known to provide containers for several different types of liquid with dispensing spouts so they dispense into their intended receiver. For example, water is provided in containers with valved spouts actuated by pressing on the top of lead-acid automotive batteries so the water is delivered directly into openings in the top of the battery.

Disclosures relative to this invention are found in U.S. Pat. Nos. 3,402,747; 3,473,886; 3,912,451; 4,011,941; 4,784,167; 4,905,819; 5,089,240; 5,127,517; 5,270,002 and 6,228,333.

SUMMARY OF THE INVENTION

In this invention, the disinfecting solution container and the contact lens container are designed so the solution container can only dispense into a contact lens container designed to mate with the solution container. This means the user cannot retrieve disinfecting solution directly from the container—it has to go into the lens container. In one way or another, the lens container provides a catalyst therein so the hydrogen peroxide decomposes at a predetermined rate, dependent mainly on hydrogen peroxide concentration and temperature. In some commercially available contact lens containers, the catalyst is located on a cap-stem assembly providing compartments for the contact lenses so the lenses and catalyst are mounted on the same support, meaning that when the lenses are placed in the container, the catalyst is also placed in the container.

The solution container is preferably non-refillable so the user cannot discharge hydrogen peroxide from a refilling container into the solution container. It is recognized that the design of the solution container and the contact lens container may vary widely.

The solution container includes a dispensing or pour opening having a valve controlling flow through the opening. The solution container is non-refillable, meaning that any fill ports are sealed and no removable caps provide access to the interior of the solution container. The valve operator is inaccessible to a human finger. By making the solution container and the lens container with a unique mating coupling, the solution container can only be mated with and dispense into the lens container.

The valve is closed when the container is upside down, i.e. in a dispensing or pouring position, either in response to the weight of liquid in the container, in response to spring pressure and/or by other techniques. The lens container, in a more-or-less upright position, mates with the solution container, in a pouring position, and includes an element to push the valve to an open position allowing discharge of liquid, preferably by gravity, from the solution container into the lens container. The user controls the amount of solution passing into the lens container simply by raising the solution container and/or lowering the lens container and thereby allowing the valve to close.

There is accordingly provided an improved method and apparatus for transferring an irritating disinfectant into a contact lens container in order to disinfect and clean contact lenses and largely preventing the user from accidentally getting the irritating solution into an eye.

It is an object of this invention to provide an improved apparatus for and method of using a contact lens disinfecting solution that is irritating to the human eye.

A further object of this invention is to provide an improved apparatus for and method of transferring a disinfecting solution from a storage container to a contact lens container.

These and other objects and advantages of this invention will become more apparent as this description proceeds, reference being made to the accompanying drawings and appended claims.

BRIEF DESCRIPTION OF THE DRAWINGS

FIG. 1 is a cross-sectional view of a solution container and a spaced lens container, the solution container being illustrated with the valve slightly raised from its normally closed position;

FIG. 2 is a cross-sectional view of the solution container and lens container when mated and transferring disinfecting solution;

FIG. 3 is an enlarged isometric cross-sectional view of the valve inside the solution container;

FIG. 4 is an enlarged isometric view of the valve of FIG. 3 in position inside a valve housing provided by the solution container;

FIG. 5 is a side view of the valve element inside the solution container;

FIG. 6 is an enlarged cross-sectional view of the solution container of FIG. 1, taken substantially along line 6-6 thereof as viewed in the direction indicated by the arrows;

FIG. 7 is an exploded, partly cross-sectional view of one embodiment of a lens container; and FIG. 8 is a side view of another embodiment of a lid assembly for a lens container.

DETAILED DESCRIPTION OF THE INVENTION

Despite the effectiveness of hydrogen peroxide, its use for disinfecting contact lenses has remained limited because of the potential for injury or pain to the user's eyes. There are several potential reasons why hydrogen peroxide may inadvertently get into the eye of a user: (1) the ineffectiveness of the catalyst to decompose hydrogen peroxide, (2) the impatience or inability of the user to leave the contact lenses in the catalyst container long enough for the catalyst to do its work, (3) the lens container does not have a catalyst to promote decomposition of the hydrogen peroxide, (4) the user wets the contact lens directly with a hydrogen peroxide solution and then, more or less immediately, places the lens in the eye and (5) the user places hydrogen peroxide directly into the eye. It will accordingly be seen that there is another requirement promoting widespread use of hydrogen peroxide for contact lens disinfecting, i.e. preventing the user from more-or-less directly putting disinfectant strength hydrogen peroxide in the eye or onto the lens.

The three most common misuses of a hydrogen peroxide disinfecting scenario are:

1. Following the neutralization process, the user rinses the contacts with full strength hydrogen peroxide from the solution bottle and then inserts the contact lenses in the eye. This is a common habit of users of non-hydrogen peroxide disinfectants, such as the so called "multipurpose" solutions that are currently commercially available. This is routinely done by users who want to re-wet their lenses before inserting them into the eye.

2. The user squirts full strength hydrogen peroxide directly into the eye from a solution container. During normal wear, contact lenses occasionally become dry and uncomfortable. Often, a contact lens wearer using a non-hydrogen peroxide or "multipurpose" solution will squirt the solution into the eye to overcome dryness and improve comfort. If this is done with a hydrogen peroxide disinfectant, a corneal burn may occur.

3. The contact lens wearer uses a contact lens storage case provided with a "multipurpose" cleaning solution instead of a catalyst included storage case intended specifically for use with hydrogen peroxide. The "multipurpose" lens cases do not include a catalyst and consequently the hydrogen peroxide is not neutralized. Again, pain and potential injury follow.

Because of the potential for patient discomfort or injury, the majority of optometrists and ophthalmologists encourage the use of so-called multipurpose solutions to clean contact lenses and thereby disinfect them of fungi and bacteria. However, much attention has been focused recently on the problems of some non-hydrogen peroxide disinfectants. At least one type of multipurpose solution is thought to allow the propagation of eye damaging parasites such as acanthamoeba keratitis. In other situations, there have been reported cases of blindness and/or the market withdrawal of some commercial "multipurpose" solutions. This has led to an increased use of hydrogen peroxide solutions which has naturally led to increased frequency of pain, discomfort and injury to people misusing hydrogen peroxide disinfectants.

Since the start of using hydrogen peroxide as a contact lens disinfectant, there has been no successful technique for eliminating the above three common misuses. It these misuses were minimized or eliminated, there would be a dramatic drop in pain and injury from hydrogen peroxide disinfectant. This will naturally lead to increased use of hydrogen peroxide disinfectants thereby substantially improving eye health of contact lens wearers. This is particularly true of many different types of users who are particularly prone to eye problems from allergies, eye-sensitive users, atypical contact lens wearers and those who generate significant amounts of heavy protein or lipid deposits on their contact lenses. In addition, if the problems of conventional hydrogen peroxide disinfectants can be overcome, eye care professionals will more likely recommend use of hydrogen peroxide thereby promoting greater eye health.

Referring to FIGS. 1-6, a solution container 10 is at least partially filled with a liquid contact lens disinfectant 12 that is irritating to the human eye. Although the disinfectant 12 may be of any suitable type, hydrogen peroxide is much preferred and is, in fact, an ideal disinfectant for contact lenses. Currently, hydrogen peroxide is believed to be the most effective disinfectant for contact lenses and its limited acceptance, to date, is due to the misuse potential of hydrogen peroxide rather than a function of its effectiveness as a disinfectant. For use in contact lenses, hydrogen peroxide is provided in an aqueous solution, typically saline, as disclosed in some detail in U.S. Pat. No. 3,912,451, to which reference is made for a more complete description of the preparation of a suitable hydrogen peroxide solution. The aqueous hydrogen peroxide may also contain other additives, such as surfactants, special cleansers for lipids or proteins, and the like.

An important feature of this invention is that the solution container 10 is non-refillable, meaning that it is sealed against disassembly and is free of closures which can be opened, such as by screw threads, friction fits or the like. The reason for making the container 10 non-refillable is that much of the protection afforded by this invention is compromised by making the container 10 openable and/or resealable. For example, if the container 10 could be opened, a user might be tempted to open the container 10 or the container used to refill the container 10 and put the disinfectant solution directly on the contact lens or into his eye.

The container 10 also includes a normally closed valve 14 including a valve housing 16 of unusual design. The valve 14 is preferably arranged so that it can substantially only be opened by the open mouth 18 of a lens container 20, meaning it is virtually impossible to dispense the contents other than into the lens container 20. By virtually impossible, it is meant that the valve 14 cannot be operated by a human finger of any size, child or adult, or by a human finger nail larger than 1/64th inch thick or shorter than 1/4 inch long. The latter requirement may be accommodated in a number of different ways, e.g. by making the valve 14 so it will not open when pushed only on one side as illustrated in FIGS. 1 and 2 or by other techniques.

Although it is preferred to design the valve 14 and valve housing 16 so the lens container 20 does not have to be modified, it is, of course, equally within the scope of this invention to provide a lens container 20 which is modified in some manner to manipulate a specifically designed valve 14 so they are a unique, mating coupling which will only transfer liquid disinfectant from the container 10 to the container 20.

The container 10 includes a bottom wall 22 having valve operating opening 24 which is preferably in the form of a closed arcuate slot such as a circle. It will be noted that the valve operating opening 24 is sufficiently small that a human finger cannot pass through it to manipulate the valve 14. The valve operating opening 24 will be seen to be sized to be slightly larger than the open mouth of the lens container 20, as explained more fully hereinafter. The bottom wall 22 includes a section 26 inside the valve operating opening 24 which provides a disinfectant dispensing opening 28, all as more fully apparent hereinafter.

The valve housing 16 is mounted on the bottom wall 22 and includes an outer cylindrical wall 30 and an inner cylindrical wall 32 providing an annulus 34 for receiving an annular valve operator 36. The inner cylindrical wall 32 is supported from the container 10 in any suitable manner, as by the provisions of struts 38 extending from the outer wall 30 through slots 40 in the valve operator 36 as shown best in FIG. 4. The struts 38 not only support the inner wall 32 but also register the valve operator 36 to prevent it from rotating and ultimately misaligning the sealing elements of the valve 14.

The bottom of the inner wall 32 is sealed against the bottom wall section 26 and includes a top wall 42 having a central opening 44 and a series of valve openings 46 as more fully explained hereinafter. The valve housing 16 also includes an interior wall 48 preferably parallel to and spaced from the bottom wall section 26 and a tube 50 provides communication between the inside of the wall 32 and the dispensing opening 28. The interior wall 48 provides a valved opening 52 allowing and preventing flow of disinfectant out of the container 10. The dispensing opening 28 is preferably too small to accommodate a human finger so the valve stem 54 cannot be intentionally unseated by extending a human finger through the opening 28. In addition, one purpose of the double walls 26, 48 is to recess a valve stem 54 so it cannot be reached by inserting a small object, such as a pencil, through the opening 28 to unseat the valve stem 54.

The annular valve operator 36 provides an annular lower slot 56 sized to closely receive the open mouth 18 of the lens container 20, a central section 58 that is box shaped in cross-section and an upper annular extension or skirt 60 that pushes on a plate 62 comprising part of a valve element 64. The skirt 60 includes the slots 40 which allow the valve operator 36 to move upwardly past the struts 38 that support the inner wall 32 as shown best in FIGS. 3 and 4. It will accordingly be seen that when the valve operator 36 is raised, the skirt 60 is raised to push on the underside of the plate 62 thereby raising the valve element 64 and opening the container 10 so liquid disinfectant flows into the lens container 20. The width and depth of the slot 56 is such that a human finger cannot enter the slot 56 and raise the valve operator 36 a sufficient distance to open the valve element 64. In the alternative, or in addition, the annular section 74 of the container 10 may be lengthened to extend below the lower end of the valve operator 36 to further isolate the valve operator 36 from intentional operation by other than the lens container 20.

The valve element 64 comprises the plate 62, one or more sealing elements 66 sealing the valve openings 46, the stem 54 having a shoulder 68 thereon and a compression spring 70 acting between the shoulder 68 and the top wall 42 of the valve housing 16. It will be seen that the spring 70 pushes the end 72 of the stem 54 into sealing engagement with the valved opening 52 and to push the plate 62 so the sealing elements 66 close the valve openings 46. Thus, the valve 14 acts to seal against downward flow of liquid disinfectant by the valve elements 46, 66 and by the valve elements 52, 72. It will accordingly be apparent that the valve 14 may be simplified by eliminating one set of the valve elements. It will also be evident that the plate 62 of the valve element 64 may be bonded to, or separate from, the skirt 60 of the valve operator 36.

The valve operator 36 is preferably made to close enough tolerances, relative to the diameter of the inner cylindrical wall 32 on which it slides, that the operator 36 is not easily operated from only one edge as may be attempted by someone pushing on it with a small object. Pushing on one edge of the operator 36 tends to tilt the operator 36, which is resisted by its close tolerance with the cylindrical wall 32, thereby effectively jamming the operator 36 and promoting operation of the valve operator 36 only by a circular object of the correct size, i.e. the open mouth 18 of the lens container 20. The close tolerance between the outside of the valve operator 36 and the inside of the outer wall 30 also prevents or minimizes leakage of disinfectant during dispensing.

It will be immediately apparent that many different valve designs are capable of discharging an aqueous hydrogen peroxide disinfectant exclusively into a lens container 20.

By stating that the transfer is only, exclusively or substantially exclusively between the solution container 10 and the lens container 20, it is meant that transfer is substantially capable only from the solution container 10 in response to mating with a element that is essentially identical to the open mouth 18 of the lens container 20.

The lens container 20 may be of any suitable design and is preferably conventional comprising an open mouth 18 for interdigitating with the valve operator 36 and a lid assembly 76 which connects with the container mouth 18 in any suitable fashion, as by the provision of threads or a friction fit. The lid assembly 76 includes one or more contact lens holders 78 supporting contact lenses inside the container 20. A catalyst body 80 is provided, either in a separate compartment 82 under a perforated divider 84 as shown in FIG. 7 or as an attachment 86 on the end of the lens holders 78 as shown in FIG. 8. In any event, the container 20 includes a catalyst therein when contact lenses are immersed in the liquid disinfectant. Although the catalyst may be of any suitable type, platinum is preferred because it is commonly used in commercially available lens containers as discussed in U.S. Pat. No. 3,912,451. The lid assembly 76 includes a conventional check valved opening 88 to allow the release of oxygen generated during the decomposition of hydrogen peroxide.

Operation of the solution container 10 and the lens container 20 should now be apparent. When the wearer is ready to remove contact lenses for cleaning, the lid assembly 76 is removed and the contact lenses placed in the holders 78. The solution container 10 is placed over the open lens container 20 and aligned so the open mouth 18 enters the slot 56 of the valve operator 36. The solution container 10 is then lowered so the valve operator 36 moves upward relative to the inner wall 32 thereby raising the plate 62 and shifting the valve element 64 to an open position. When the lens container 20 contains sufficient liquid disinfectant, the solution container 10 is raised allowing the spring 70 to push the valve stem 54 relatively downward to close the valve elements 46, 66 and 52, 72 and thereby stop flow of the liquid disinfectant. The lens container 20 is closed with the lid assembly 76 so the contact lenses and any catalyst on the lid assembly 76 are immersed in the liquid disinfectant. The contact lenses are left in the container 20 for a time period sufficient to allow the catalyst to decompose the liquid disinfectant thereby lowering its concentration to a level that is easily tolerated by the human eye.

It will accordingly be seen that this invention eliminates many of the potential misuses of irritating liquid disinfectants.

Although this invention has been disclosed and described in its preferred forms with a certain degree of particularity, it is understood that the present disclosure of the preferred forms is only by way of example and that numerous changes in the details of operation may be resorted to without departing from the spirit and scope of the invention as hereinafter claimed.

I claim:

1. A method of protecting an eye of a contact lens wearer from the effects of an irritating liquid disinfectant, comprising providing an aqueous solution of the disinfectant in a supply container having a normally closed dispensing opening adapted to be opened exclusively by coupling with a contact lens container having an unobstructed filling opening therein;

configuring the supply container and the contact lens container so that transferring the liquid disinfectant from the supply container to the contact lens container can be accomplished only when the supply container is coupled to the contact lens container whereby a user cannot retrieve disinfecting solution directly from the supply container except into the lens container;

transferring the liquid disinfectant from the supply container dispensing opening into the contact lens container through the filling opening;

uncoupling the supply container from the contact lens container and exposing an interior of the contact lens container to an exterior thereof and then closing the filling opening; and then immersing at least one contact lens in the contact lens container having therein a catalyst for decomposing the liquid disinfectant;

maintaining the at least one contact lens in contact with the disinfectant until the lenses are substantially disinfected.

2. The method of claim 1 wherein the disinfectant is aqueous hydrogen peroxide.

3. The method of claim 1 wherein the supply container includes a valve, a valve operator for manipulating the valve and an annular slot providing access to the valve operator and wherein the lens container provides an open mouth sized and shaped to be received in the annular slot for manipulating the valve operator and wherein the mating step comprises aligning the annular slot with the open mouth and fluidly communicating the open mouth of the lens container with the supply container dispensing opening and manipulating the valve operator with the lens container.

4. The method of claim 3 wherein the supply container dispensing opening is circular and the open mouth of the lens container is circular.

5. A method of protecting the eye of a contact lens wearer from an irritating liquid disinfecting solution comprising providing a disinfectant solution container and a contact lens container, the disinfectant solution container comprising a dispensing opening having a normally closed valve therein movable between an open and a closed position and a valve operating opening separated from said dispensing opening and a valve actuator in said valve operator opening for moving the valve to the open position in response to inserting an element of a lens container into the valve operating opening, the operating opening being a slot of a size inaccessible by a human finger whereby a user cannot retrieve disinfecting solution directly from the supply container except into the lens container;

the contact lens container comprising an inlet opening for receiving hydrogen peroxide from the solution container in an upright position of the lens container, the inlet opening having an open mouth provided with said element sized and adapted to pass into the slot of the solution container for operating the valve actuator to actuate the valve to its open position and a catalyst in the lens container for accelerating the decomposition of hydrogen peroxide, mating said solution container with said contact lens container thereby actuating said valve to transfer, by gravity, solution from the solution container to the contact lens container;

placing at least one contact lens in the contact lens container for a time sufficient to allow the catalyst in the lens container to decompose the liquid disinfecting solution.

6. A method of protecting an eye of a contact lens wearer from the effects of a liquid irritating disinfectant, comprising providing a first container at least partially filled with an aqueous disinfectant solution and having an outlet including a valve for dispensing the solution, the valve having an operator for opening the valve, the operator having a contact surface being inaccessible by a human finger from an exterior of the first container whereby a user cannot retrieve disinfecting solution directly from the supply container except into the lens container and being exclusively operable by coupling with a second container;

providing the second container for the contact lens, the second container having a passage providing access to an interior of the second container for receiving the contact lens, said passage defining an open mouth adapted for contact with said contact surface in the first container for exclusively manipulating the valve from a closed position to an open position and thereby discharging liquid from the first container to the second container;

placing the lens in the second container having therein a catalyst for decomposing the disinfectant into a liquid that is not irritating to the human eye;

placing the open mouth of the second container into fluid communication with the outlet of the first container, opening the valve with the open mouth of the second container and discharging disinfectant solution from the first container into the second container;

removing the second container from the first container;

exposing an interior of the second container to an exterior thereof and then closing the access passage; then allowing the disinfectant solution to clean the contact lens and be decomposed by the catalyst into a non-irritating liquid.

7. The method of claim 6 wherein the disinfectant solution is aqueous hydrogen peroxide.

8. A method of protecting the eyes of a contact lens wearer from the effects of hydrogen peroxide disinfectant, comprising providing hydrogen peroxide in a non-refillable container having an outlet with a discharge valve therein, said discharge valve adapted to be opened by an actuating mechanism disposed separate from said outlet and being inaccessible from the exterior of said non-refillable container, said actuating mechanism being exclusively actuated by coupling a filling inlet of a contact lens container thereto, whereby a user cannot retrieve disinfecting solution directly from the supply container except into the lens container;

coupling the inlet opening of the lens container with the actuating mechanism in the non-refillable container and transferring the hydrogen peroxide from the outlet of the non-refillable container into the inlet opening of the contact lens container;

uncoupling the lens container and the non-refillable container and exposing an interior of the lens container to an exterior thereof;

preventing dispensing of the hydrogen peroxide from the non-refillable container except into the contact lens container;

immersing at least one contact lens in the lens container; and then maintaining the at least one contact lens in contact with the disinfectant until the at least one contact lens is substantially disinfected; and decomposing the hydrogen peroxide with a catalyst in the lens container.

9. A method of protecting the eyes of a contact lens wearer from the effects of hydrogen peroxide disinfectant, comprising transferring hydrogen peroxide from an outlet of a supply container having a normally closed valve therein into a contact lens container, said supply container having a valve actuator disposed separate from said outlet, said transferring occurring through direct mating of said containers whereby said valve actuator actuates said valve to its open position, said valve actuator being inaccessible by a human finger from the exterior of said supply container whereby a user cannot retrieve disinfecting solution directly from the supply container except into the lens container; and immersing at least one contact lens in the lens container having therein a catalyst, exposing an interior of the lens container to an exterior thereof; and then maintaining the at least one contact lens in contact with the disinfectant until the lens is substantially disinfected; and decomposing the hydrogen peroxide with the catalyst.

10. The method of claim 9 wherein the lens container provides an open mouth and the supply container comprises a valve having a valve operator for dispensing hydrogen peroxide disinfectant, the valve operator being manipulated by the open mouth of the contact lens container and wherein the transferring step comprises inserting the open mouth of the lens container into the valve operator and shifting the valve from a closed position to an open position.

11. The method of claim 1 wherein the transferring step comprises transferring the liquid disinfectant by gravity from the supply container into the contact lens container.

12. The method of claim 5 further comprising, after the mating step, unmating the disinfectant solution container from the contact lens container and exposing the interior of the lens container to the exterior thereof; and wherein the placing step comprises placing at least one contact lens in the contact lens container; and then allowing the disinfectant solution to clean the contact lens.

13. The method of claim 6 wherein the discharging step comprises transferring the liquid disinfectant by gravity from the first container into the second container.

14. The method of claim 8 wherein the transferring step comprises transferring the hydrogen peroxide by gravity from the non-refillable container into the contact lens container.

15. The method of claim 9 wherein the transferring step comprises transferring the hydrogen peroxide by gravity from the supply container into the contact lens container.

16. The method of claim 10 wherein the supply container is a non-refillable container.

* * * * *